United States Patent [19]

Kawashima et al.

[11] Patent Number: 5,213,758
[45] Date of Patent: May 25, 1993

[54] METHOD AND APPARATUS FOR TREATING MEDICAL WASTES

[75] Inventors: Norihiro Kawashima, Akashi; Takashi Kameda, Kobe; Shigenori Kataoka, Kobe; Koichi Noma, Kobe; Eikichi Tajima, Kobe; Hidehumi Ikegami, Asaka, all of Japan

[73] Assignee: Kawasaki Jukogyo Kabushiki Kaisha, Kobe, Japan

[21] Appl. No.: 691,818

[22] Filed: Apr. 26, 1991

[30] Foreign Application Priority Data

Apr. 27, 1990 [JP] Japan .................................. 2-113655
Jul. 9, 1990 [JP] Japan .................................. 2-181093

[51] Int. Cl.$^5$ .......................... A61L 2/12; A61L 2/24
[52] U.S. Cl. .......................... 422/21; 422/38; 422/294; 422/307; 423/DIG. 18; 588/900; 588/210; 588/212; 588/227
[58] Field of Search .................. 422/21, 38, 294, 307; 423/DIG. 18, DIG. 20; 219/10.55 B; 588/900, 210, 212, 227

[56] References Cited

U.S. PATENT DOCUMENTS

| 3,670,891 | 6/1972 | Allen | 422/21 |
| 3,674,422 | 7/1972 | Gray | 422/21 |
| 3,753,651 | 8/1973 | Boucher | 422/21 |
| 4,552,720 | 11/1985 | Baker, Sr. et al. | 422/294 |
| 4,891,239 | 1/1990 | Dudley et al. | 422/21 |
| 4,992,217 | 2/1991 | Spinello | 422/294 |
| 4,999,471 | 3/1991 | Guarneri et al. | 422/21 |
| 5,035,858 | 7/1991 | Held et al. | 422/27 |

FOREIGN PATENT DOCUMENTS

| 0430898 | 11/1985 | European Pat. Off. |
| 1-176486 | 7/1989 | Japan . |
| 1-263410 | 10/1989 | Japan . |
| 1-315383 | 12/1989 | Japan . |
| 50626496 | 6/1979 | U.S.S.R. | 422/21 |
| 8801182 | 2/1988 | World Int. Prop. O. . |
| 9014847 | 6/1989 | World Int. Prop. O. . |

Primary Examiner—Robert J. Warden
Assistant Examiner—Laura E. Collins
Attorney, Agent, or Firm—Leydig, Voit & Mayer

[57] ABSTRACT

Medical wastes are placed in a medical waste container which is then placed in a closed apparatus body. The container is heated by a heater so that the medical wastes are sterilized and melted or softened. The container containing the medical wastes is then compressed and molded by a compression device. The compression-molded product containing the medical wastes and the container is then discharged from a door of the apparatus body. Alternatively, medical wastes are heat-sterilized by operating a microwave generator. The microwave generator is controlled by detecting the concentration of the combustible gases contained in the exhaust gases discharged from a closed apparatus body, the concentration of hydrogen chloride gas and/or a ratio of reflected power to incident power by using a power monitor connected to a waveguide of the microwave generator. At the same time, hot air can also be circulated.

9 Claims, 5 Drawing Sheets

METHOD AND APPARATUS FOR TREATING MEDICAL WASTES

BACKGROUND OF THE INVENTION

The present invention relates to a method and apparatus for treating medical implements waste involving used hemodialyzers, used syringes, used injection needles, used gauze, used vessels and so on.

In order to prevent infectious medical wastes discharged from hospitals, dialysis facilities and the like from causing secondary infection, a guideline for specifying the method of treating such wastes was published by the Welfare Ministry of Japan on Nov. 7, 1989 and enforced on Apr. 1, 1990. This guideline imposes duty on hospitals, dialysis facilities and the like to sterilize the medical implements waste discharged therefrom, as a general rule.

Japanese Patent Unexamined Publication No. 1-176486 discloses a treatment method and apparatus in which used synthetic resin syringes and injection needles are contained in a heat-resistant container, heated and melted at a predetermined temperature for sterilization and then cooled for solidification.

Japanese Utility Model Unexamined Publication No. 1-144040 discloses an apparatus for heat-sterilizing wastes in which wastes are heat-sterilized and then crushed by a crusher for reducing the volume.

Japanese Patent Examined Publication No. 51-25470 discloses an apparatus for treating plastic wastes in which plastic wastes are placed in a cylinder, heated by a heater contained in the bottom plate of the cylinder and a piston and compressed, and, at the same time, integrally molded by mainly melting the surfaces.

Japanese Patent Unexamined Publication No. 1-315383 discloses an apparatus in which used disposable syringes are heat-sterilized by an electric heater and a far infrared heater, both of which are provided in the side and bottom surfaces of a heating furnace. A method is also disclosed as an embodiment in which wastes to be treated are melted in a heat-resistant container, cooled and then discharged as one product containing needles.

Japanese Patent Unexamined Publication No. 1-263410 discloses an apparatus for heating wastes by microwaves, and drying, burning and then ashing the wastes.

When wastes such as hemodialyzers and the like, which are made of plastics having different melting points, are treated by using the treatment method and apparatus disclosed in Japanese Patent Unexamined Publication No. 1-176486, volume reduction (molding) is insufficiently effected because many wastes remain unmelted at the treatment temperature. When wastes containing polyvinyl chloride are treated, since HCl gas is generated at 190° C. or more, off-gas treatment is required.

In addition, the method of crushing by a crusher in the apparatus for heat-sterilizing wastes disclosed in Japanese Utility Model Unexamined Publication No. 1-144040 has the disadvantages that the effect of reducing the volume of wastes is not always excellent, and that there are needs for the maintenance of the crusher cutter and for many power sources generating great noise and vibration.

The apparatus for treating plastic wastes disclosed in Japanese Patent Examined Publication No. 51-25470 has the disadvantage that, since the apparatus is proposed on the basis of the idea that only the surfaces of wastes are coated with a melt, without the intention of sterilizing the wastes, the molded product has poor stability.

The apparatus disclosed in Japanese Patent Unexamined Publication No. 1-315383 has the disadvantage that, since large wastes to be treated such as used hemodialyzers, which contain water, cannot be easily heated only by circulating hot air, the wastes are insufficiently sterilized, and much time is required for treatment. In addition, because a hemodialyzer is made of various kinds of plastics, melted and unmelted portions are mixed at a certain treatment temperature, and thus a reduction in volume cannot be sufficiently effected.

Further, when wastes to be treated such as used hemodialyzers, tubes and the like, which are made of various kinds of plastics, are treated by the apparatus disclosed in Japanese Patent Unexamined Publication No. 1-263410, since toxic gas such as hydrogen chloride or the like is generated, it is necessary to take into account the material for the apparatus and the treatment of the exhaust gas, resulting in the complication of the apparatus. There are also the disadvantages that the method of reducing the volume by ashing using microwaves requires much power, and the apparatus itself is heated to a high temperature and is thus unsuitable for installation in hospitals and clinics.

On the other hand, medical waste products contain various kinds of plastics. For example, when the ratios of the raw materials which form a hemodialyzer set including a blood circuit (tube and the like), a syringe, a physiologic saline container and so on were measured by analysis, the following results were obtained:

| | | |
|---|---|---|
| (1) Polyvinyl chloride | | 50% by weight |
| (2) Polystyrene or polycarbonate | | 30% by weight |
| (3) Cellulose or synthetic film | | 5% by weight |
| (4) Polyethylene, polypropylene or silicone | | 5% by weight |
| (5) Polyurethane and stainless steel | | 10% by weight |

The properties of main plastics of the above materials are given in Table 1.

TABLE 1

| Material Name | Melting Point | Softening Point | Note |
|---|---|---|---|
| Polyvinyl chloride | about 170° C. | 65–85° C. | HCl gas is generated at 190° C. or more. |
| Polystyrene | about 230° C. | 90–102° C. | Deformation temperature; 70–100° C. (ASTM D648) Softening point; 97–100° C. (ASTM D1525-58T) |
| Polycarbonate | about 230° C. –260° C. | 145–165° C. | Deformation temperature (ASTM D648) 130–136° C. (18.6 kg/cm²) 136–142° C. (4.6 kg/cm²) |
| (Medium-density) Polyethylene | about 120° C. | | Softening point; 100–120° C. (ASTM D1525) Deformation temperature; 50–66° C. (ASTM D648) |

TABLE 1-continued

| Material Name | Melting Point | Softening Point | Note |
|---|---|---|---|
| Polypropylene | about 180° C. | 96–105° C. (ASTM D1525) | |

Remarks: ASTM (American Society for Testing and Materials)

In addition, a relation between the heating temperature and the gases generated were examined for a polyvinyl chloride tube (blood circuit) by the method below. A glass bottle having an internal volume of 1 l and a heat insulator provided at the bottom was disposed in an intermediate portion in a drying furnace having an electric heater provided at the inner bottom thereof. A blood circuit (main component: polyvinyl chloride) was placed in the glass bottle and sealed by a stopper. A thermometer and a sampling tube were passed through the stopper so that the temperature at the inner bottom of the glass bottle and the concentrations of the gases generated were examined. The results obtained are shown in Table 2. The hydrogen chloride gas generated was detected by using detector tubes with measurement ranges of 1 to 20 ppm and 20 to 500 ppm, and the carbon monoxide gas generated was detected by using a detector tube with a measurement range of 25 to 500 ppm.

TABLE 2

| Temperature [°C.] | Concentration of gas generated | |
|---|---|---|
| | HCl [ppm] | CO [ppm] |
| 165 | 2 | 60 |
| 170 | 2 | 50 |
| 175 | 2 | 60 |
| 180 | 3 | 120 |
| 185 | 200 | 500 or more |
| 190 | 500 or more | |

SUMMARY OF THE INVENTION

The present invention has been achieved in consideration of the above problems, and it is an object of the present invention to provide a method and apparatus for treating medical implements waste in which medical wastes containing at least one kind of plastic (synthetic resin and rubber) are heat-sterilized by a far infrared heater, an electric heater, microwaves or the like at a predetermined temperature for a predetermined time and, at the same time, at least one kind of plastic is melted or softened, and the treated wastes are then reduced in the volume by compression, molding and solidification to produce a shape having excellent handling properties.

It is another object of the present invention to provide a method and apparatus in which infectious wastes containing plastics are heat-sterilized by combination of microwave heating and hot air circulation heating, and the microwave output is controlled by detecting the concentrations of the combustible gases (carbon monoxide, hydrocarbon and the like) and hydrogen chloride gas contained in the waste gases and/or a ratio of the reflected power to the incident power, which ratio is detected by the power monitor connected to the waveguide of a microwave generator.

In order to achieve the objects, a method of treating medical implements waste in accordance with the present invention comprises the steps of heat-sterilizing medical implements waste containing plastics and, at the same time, melting or softening part or the whole of the plastics, and then reducing the volume by compression.

An apparatus for treating medical wastes in accordance with the present invention comprises a closed apparatus body provided with an open-close door and an exhaust port, a medical waste container disposed in the closed apparatus body, a heater disposed around the medical waste container, and a compression device for compressing the container containing medical implements waste so as to reduce the volume thereof.

DESCRIPTION OF THE PREFERRED EMBODIMENTS

Figure 1:
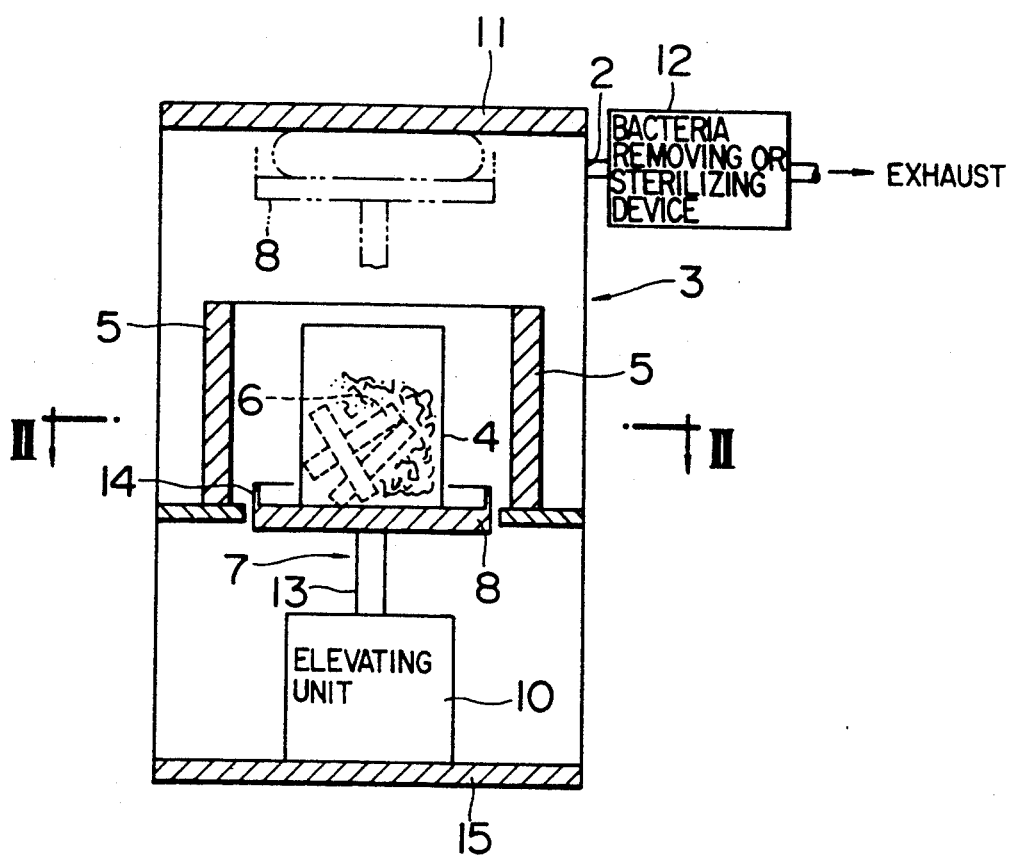
FIG. 1 is a longitudinal sectional view of an apparatus for treating medical implements waste in accordance with the present invention.

Preferred embodiments of the present invention are described below with reference to the attached drawings. In the drawings, the same reference numeral denotes the same or equivalent member.

Figure 2:
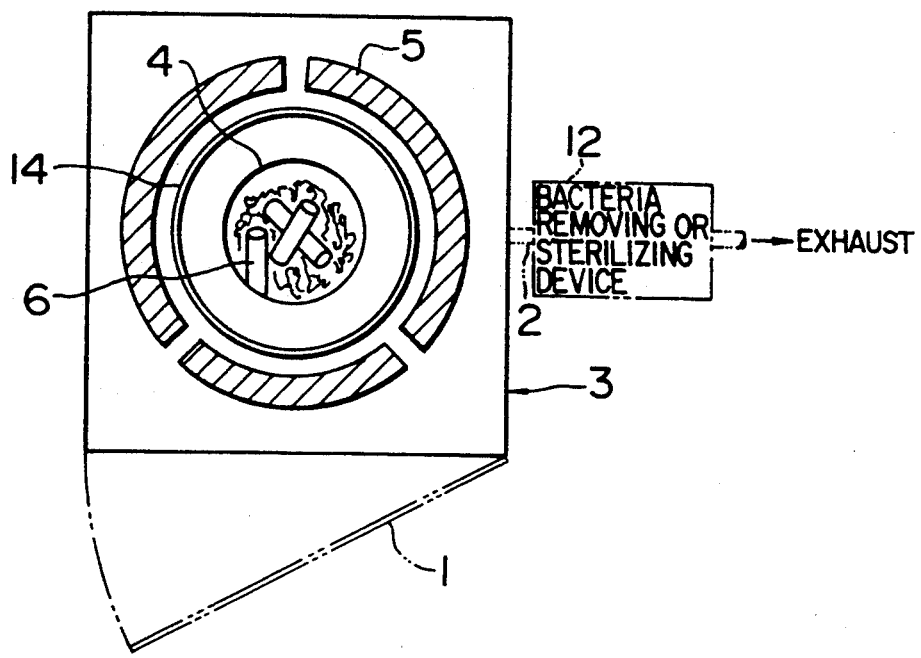
FIG. 2 is a sectional view taken along the line II—II in FIG. 1.

The apparatus for treating medical implements waste in the embodiment of the present invention shown in FIGS. 1 and 2 comprises a closed apparatus body 3 provided with an open-close door 1 and an exhaust port 2, a medical waste container 4 disposed in the closed apparatus body 3, a heater 5 disposed around the medical waste container 4 and a compression device 7 for compressing the medical waste container 4 containing medical implements waste so as to reduce the volume thereof.

Figure 6:
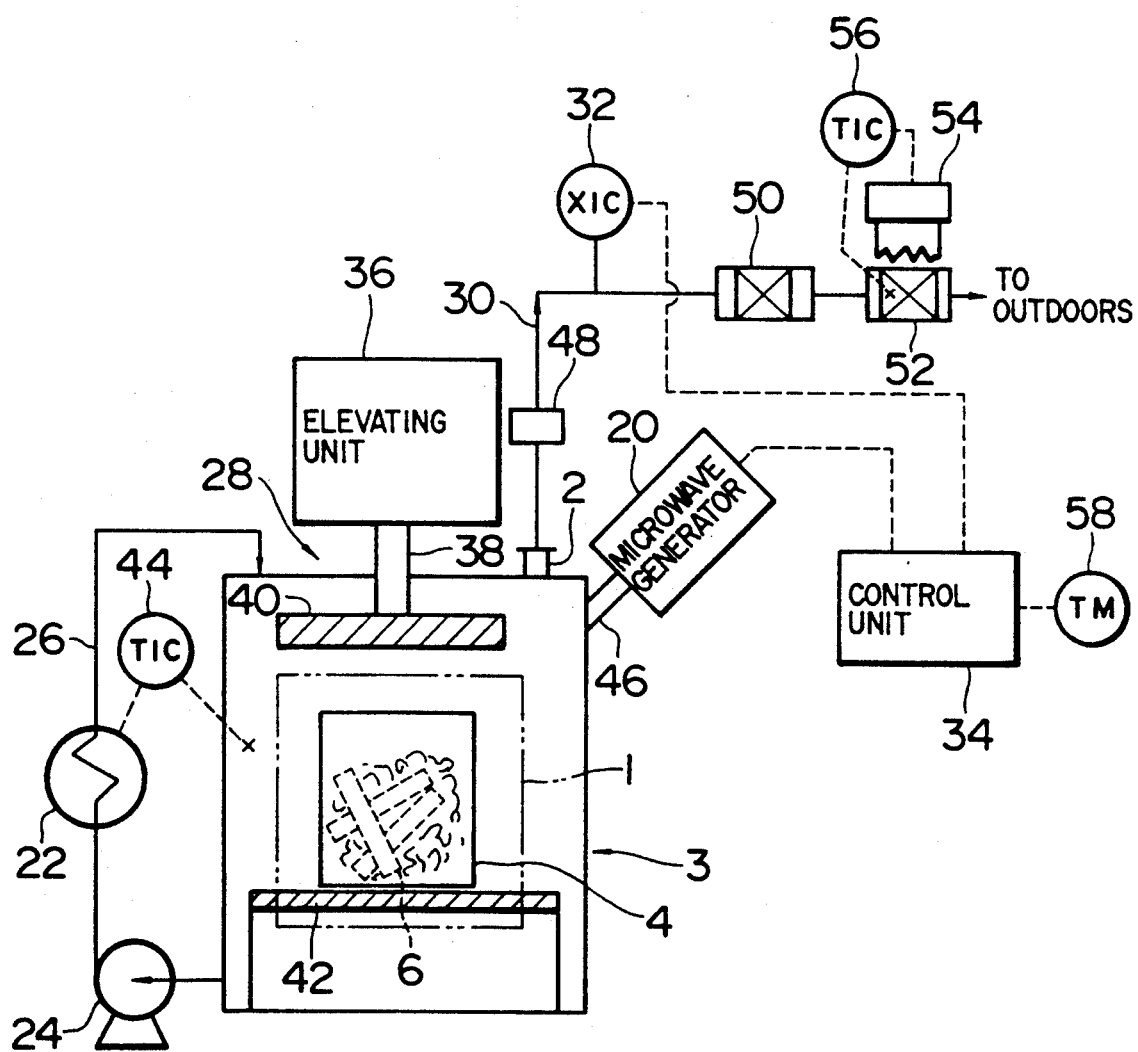
FIG. 6 is a sectional view of still other embodiment of the present invention.
Figure 7:
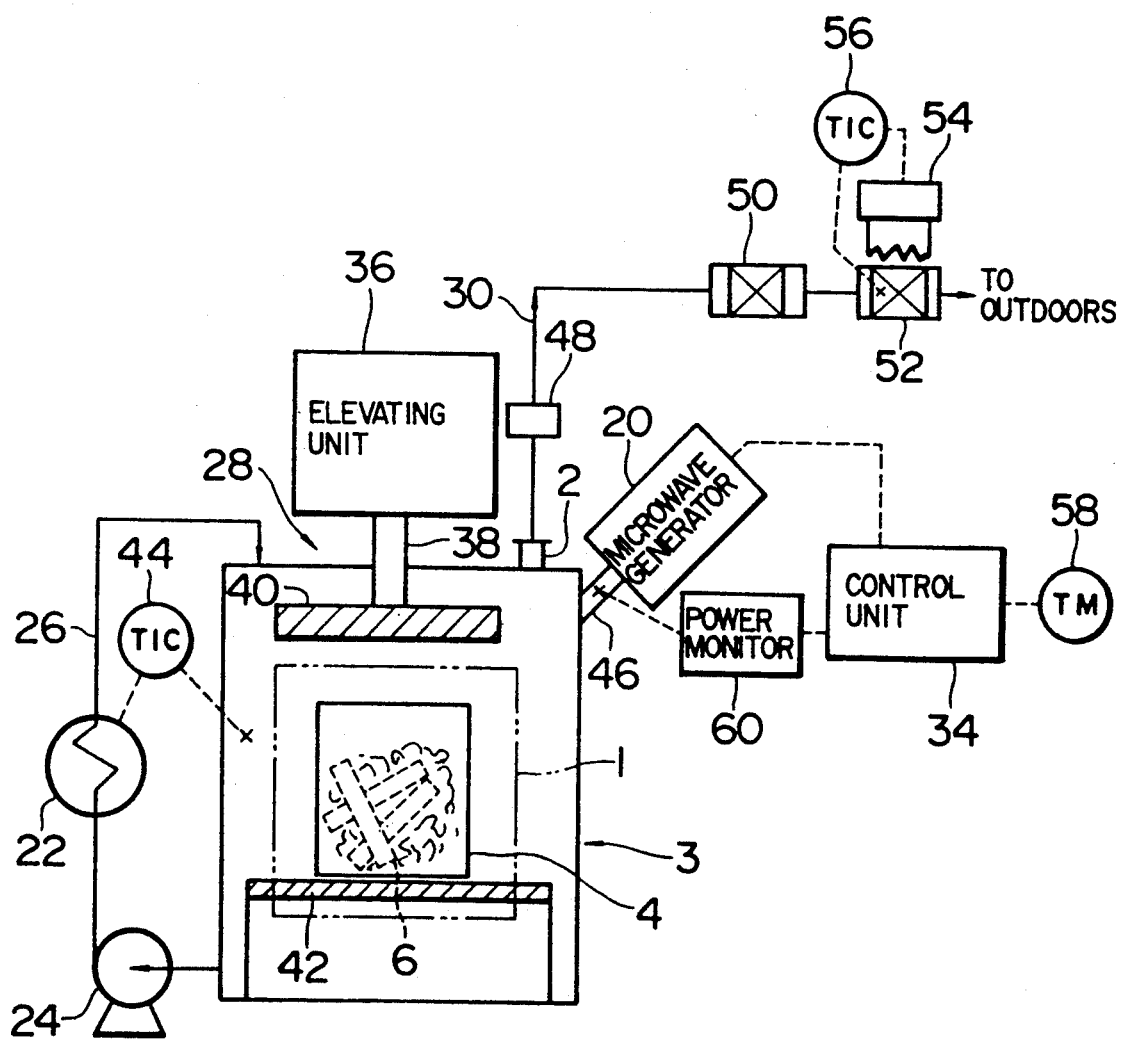
FIG. 7 is a sectional view of a further embodiment of the present invention.

Although a heating device which employs a far infrared heater, an electric heater or microwaves is used as the heater 5, it is preferable to use a heater which employs the combination of microwave heating and hot-air circulation heating, as shown in FIGS. 6 and 7.

The medical waste container 4 must maintain its shape or the function of containing medical implements waste for a while during the time the container 4 is melted or softened by heating. A plastic or corrugated fiberboard container or the like is thus preferably used as the container 4.

When the apparatus for treating medical implements waste shown in FIGS. 1 and 2 is used, the medical waste container 4 comprising a bag or a container containing medical implements waste 6 is loaded on a compression plate 8 which also serves as a pedestal and which is disposed in the closed apparatus body 3. The medical waste container 4 is then heated at a predetermined temperature for a predetermined time so that the medical implements waste 6 are sterilized and melted or softened.

When the medical implements waste contain polyvinyl chloride, since HCl gas is generated if the heating temperature exceeds 190° C., the heating temperature is preferably as lower than 190° C. as possible, for example, 110° to 190° C. If a device for treating HCl gas is provided, the heating temperature may be over 190° C.

The heating time must be a time required for complete sterilization which is the main object of heating and depends upon the heating temperature. For example, when the heating temeprature is 180° C., the sterilization time is preferably within the range of 10 to 60 minutes.

An elevating unit 10 is then operated for elevating the medical implements waste 6 and the container 4 which are melted or softened (referred to as "treated wastes" hereinafter), so that the treated wastes are compressed by pushing them on a top plate 11, as shown by two-dot chain lines in FIG. 1. The top plate 11 preferably has a structure in which a jacket is provided or a cooling tube is passed therethrough for cooling the treated wastes. This structure prevents the treated wastes from adhering to the top plate 11. The elevating unit 10 is operated by hydraulic pressure, pneumatic pressure or electric power.

The elevating unit 10 is then operated so that the treated wastes are downwardly moved. After the treated wastes have been naturally cooled or forced to cool by a fan, the integrally molded product is discharged from the open door 1. The apparatus can be configured so that the treated wastes can be divided into several parts for molding or so that the treated wastes can be automatically discharged by using a push rod or the like.

A bacteria removing filter such as a HEPA (High Efficiency Particulate Air) filter or the like or a bacterial removing or sterilizing device 12 is connected to the exhaust port 2 so as to prevent scattering of bacteria contained in the gases discharged from the medical implements waste in the initial stage of heating. In fact, the HEPA filter is not singly used because clogging easily occurs, and the HEPA filter is used in combination with filters called a prefilter and a medium-efficiency filter, both of which have rough meshes. In this application, the HEPA filter includes all the filters. Reference numeral 13 denotes a push rod, and a compression device 7 comprises the push rod, the elevating unit 10 and the compression plate 8 serving as a pedestal. Reference numeral 14 denotes a weir for preventing a melt from spilling, and reference numeral 15 denotes a bottom plate.

Figure 3:
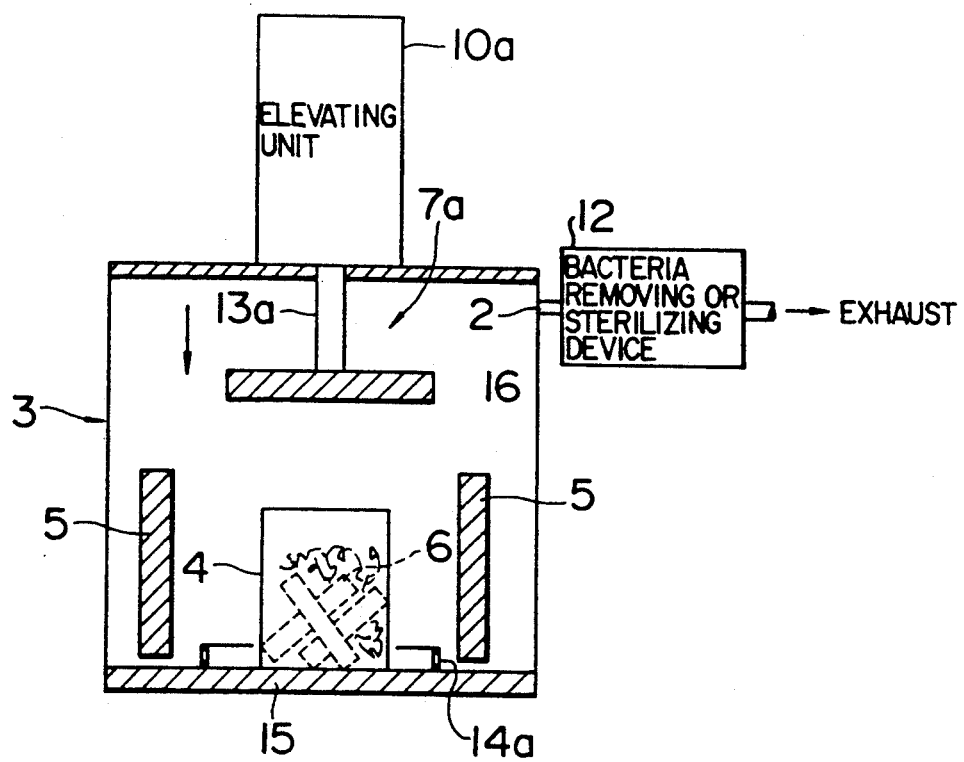
FIG. 3 is a sectional view of another embodiment of the present invention.

In the embodiment shown in FIG. 3, a compression device comprising an elevating unit 10a, a push rod 13a and a compression plate 16 is provided on the upper side of the closed apparatus body 3 so that the treated wastes are downwardly compressed. Reference numeral 14a denotes a weir. The other members and function are the same as those in the embodiment shown in FIGS. 1 and 2.

Figure 4:
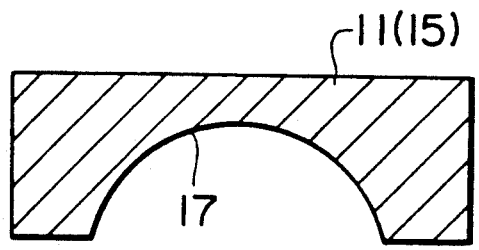
FIG. 4 is a sectional view of an example of the top plate or bottom plate in accordance with an embodiment of the present invention.

The top plate 11 shown in FIG. 1 can be formed into a shape having a concave surface 17 on the compression side, as shown in FIG. 4. This shape is reversed so that it can be applied to the bottom plate 15 shown in FIG. 3. The other members are the same as those in the embodiment shown in FIGS. 1 to 3.

Figure 5:
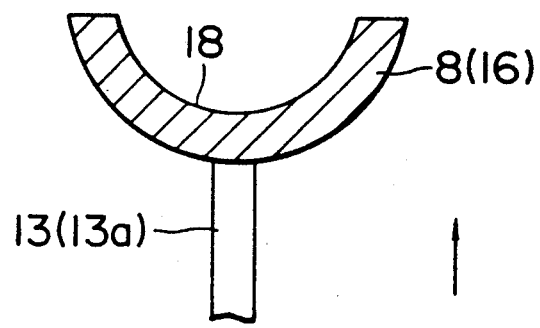
FIG. 5 is a sectional view showing the shape of a compression plate connected to a push rod in accordance with an embodiment of the present invention.

The compression plate 8 shown in FIG. 1 may have a shape having a concave surface 18 on the compression side, as shown in FIG. 5. This shape is reversed so that it can be applied to the compression plate 16 shown in FIG. 3. In the drawings, an arrow shows the compressing direction. The other members are the same as those in the embodiment shown in FIGS. 1 to 3.

In addition, a heater and/or a cooling coil may be provided by burying it in or winding on the surface of the top plate 11 and/or the compression plates 8, 16.

The embodiment shown in FIG. 6 comprises a closed apparatus body 3 provided with an open-close door 1 and an exhaust port 2; a medical waste container 4 disposed in the closed apparatus body 3; a microwave generator 20 connected to the closed apparatus body 3 for applying microwaves to the medical waste container 4; a circulating hot air line provided outside the closed apparatus body 3 and having a heater 22 and a circulating blower 24, both of which are provided for heating the medical waste container 4; a compression device 28 for reducing, by compression, the volume of the medical waste container 4 containing medical implements waste 6; a combustible gas concentration-indicating controller 32 or a combustible gas concentration controller, which is provided on an exhaust gas conduit 30 connected to the exhaust port 2; and a control unit 34 connected to the combustible gas concentration-indicating controller 32 or combustible gas concentration controller and the microwave generator 20 so as to control the microwave generator 20 on the basis of the concentration of the combustible gases generated. In this apparatus, medical implements waste containing plastics are heat-sterilized by circulating hot air, as well as applying a microwave to the wastes, and the concentration of the combustible gases generated from the medical implements waste is detected for controlling the microwave output.

In FIG. 6, reference numeral 36 denotes an elevating unit; reference numeral 38, a push rod; and reference numeral 40, a compression plate; all of which comprise the compression device 28. Reference numeral 42 denotes a bottom plate; reference numeral 44, a temperature indicating controller; and reference numeral 46, a waveguide. It is preferable that part or the whole of the heat-sterilized plastics is melted or softened and then compressed by the compression device 28 so that the volume is reduced.

The exhaust gas conduit 30 comprises a HEPA filter 48 for removing bacteria (preventing scattering of bacteria), an alkali packed portion 50 for removing acid gases such as HCl and the like and a catalyst packed portion 52 which is packed with an oxydation catalyst (for example, an alumina-carrying platinum catalyst) for removing an odor and preventing scattering of bacteria. The order of the portions 48, 50 and 52 shown in the drawing is only an example and can be appropriately changed. Reference numeral 54 denotes a heater, and reference numeral 56 denotes a temperature-indicating controller.

A timer 58 is connected to the control unit 34, the longest operating time of the microwave generator 20 being previously set in the timer 58. Namely, when the intensity of the microwaves generated is controlled, the time for high intensity is controlled.

The other members and function are the same as those in the embodiment shown in FIGS. 1 to 5.

The embodiment shown in FIG. 7 comprises a closed apparatus body 3 provided with an open-close door 1 and an exhaust port 2; a medical waste container 4 disposed in the closed apparatus body 3; a microwave generator 20 connected to the closed apparatus body 3 for the purpose of applying microwaves to the medical waste container 4; a circulating hot air line 26 provided outside the closed apparatus body 3 and having a heater 22 and a circulating blower 24, both of which are provided for heating the medical waste container 4; a compression devide 28 for reducing, by compression, the volume of the medical waste container 4 containing medical wastes 6; a power monitor 60 connected to the waveguide 46 of the microwave generator 20; and a control unit 34 connected to the power monitor 60 and the microwave generator 20 for the purpose of controlling the microwave generator 20 on the basis of the ratio of the reflected power to the incident power, which ratio is detected by the power monitor 60; wherein medical implements waste containing plastics are heat-sterilized by circulating hot air and applying microwaves thereto, and the ratio of the reflected power to the incident power is detected by the power monitor for controlling the microwave output.

In this embodiment, the power monitor 60 is connected to the waveguide 46 so as to be connected to the control unit 34 in place of the combustible gas concentration-indicating controller 32 provided on the exhaust gas conduit 30.

In this embodiment, the power monitor 60 for monitoring the incident power directed from the microwave generator 20 to the medical waste container 4 in the closed apparatus body 3 and the reflected power returned from the medical waste container 4 is used as a sort of "means for monitoring the water content remaining in the treated wastes".

The ratio of the reflected power to the incident power, which ratio is detected by the power monitor of this embodiment, is used in place of the output signal of combustible gases in the embodiment shown in FIG. 6 or in combination therewith.

When the treated wastes contain large quantities of water, because microwaves are mainly absorbed by water, the ratio of the reflected power to the incident power (reflected power/incident power) is decreased. However, since the amount of the water absorbed decreases as the water content decreases by evaporation, the ratio of reflected power/incident power is increased. This characteristic is employed as means for monitoring the amount of the remaining water, i.e., means for monitoring a degree of drying.

When the content of the remaining water is decreased, microwaves show absorption characteristics depending upon the plastic materials contained in the wastes, and this causes local overheating. For example, microwaves are easily absorbed by polyvinyl chloride, while it is not easily absorbed by Teflon and polypropylene.

Figure 8:
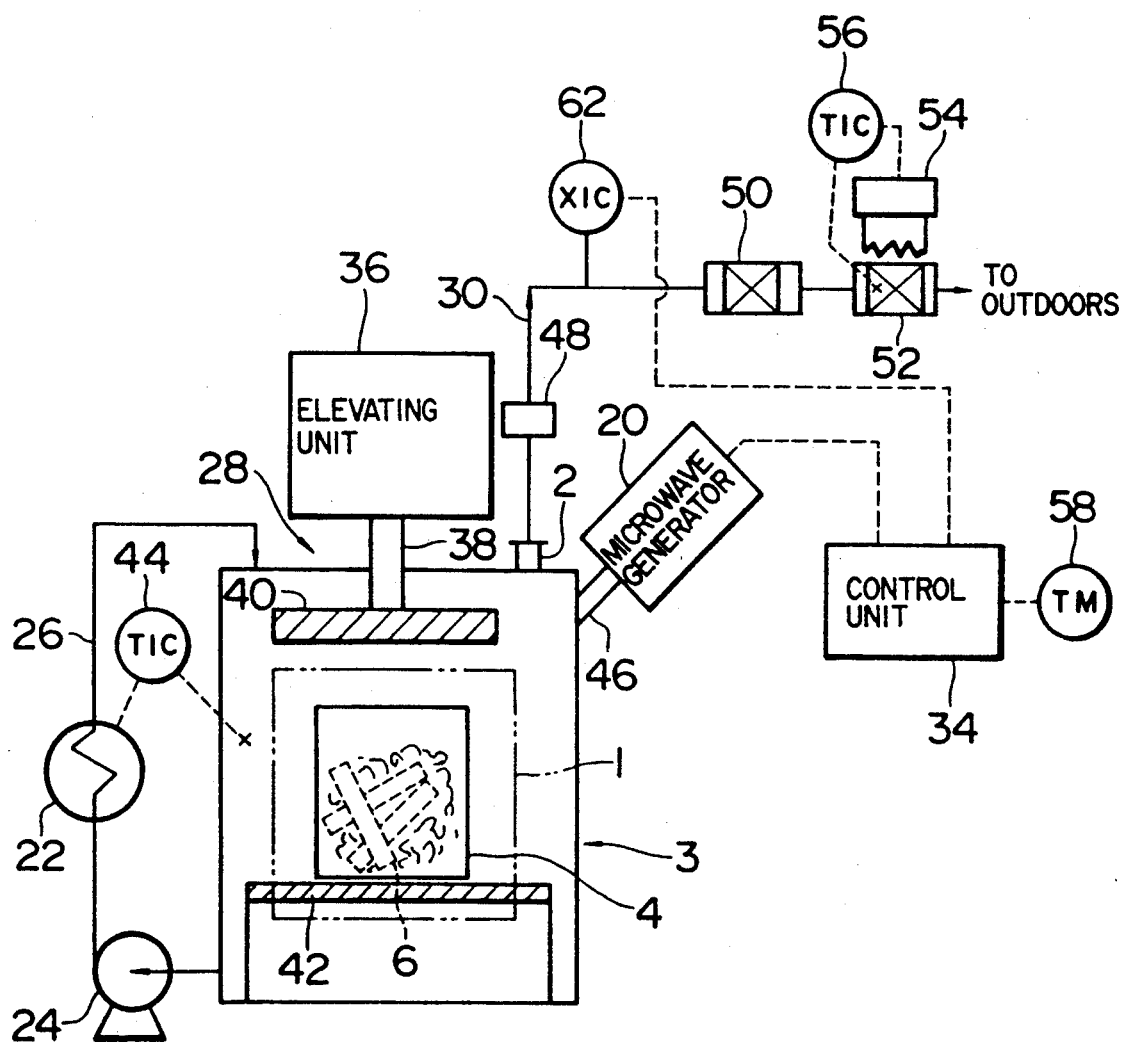
FIG. 8 is a sectional view of a still further embodiment of the present invention.

The embodiment shown in FIG. 8 comprises a closed apparatus body 3 provided with an open-close door 1 and an exhaust port 2; a medical waste container 4 disposed in the closed apparatus body 3; a microwave generator 20 connected to the closed apparatus body 3 for the purpose of applying microwaves to the medical waste container 4; a criculating hot air line 26 provided outside the closed apparatus body 3 and having a heater 22 and a circulating blower 24, both of which are provided for heating the medical waste container 4; a compressing device 28 for reducing by compression the volume of the medical waste container 4 containing the medical implements waste 6; a hydrogen chloride gas concentration-indicating controller 62 or a hydrogen chloride gas concentration controller provided on the exhaust gas conduit 30 connected to the exhaust port 2; and a control unit 34 connected to the hydrogen chloride gas concentration-indicating controller 62 or the hydrogen chloride gas concentration controller and the microwave generator 20 for the purpose of controlling the microwave generator 20 on the basis of the concentration of hydrogen chloride gas; in which medical waste containing plastics are heat-sterilized by circulating hot air and applying microwaves thereto, and the concentration of the hydrogen chloride gas generated from the medical implements waste is detected for controlling the microwave output.

The other members and function are the same as those in the embodiment shown in FIG. 6.

In the embodiment shown in FIG. 8, the hydrogen chloride gas concentration-indicating controller 62 is provided on the exhaust gas conduit 30 in place of the combustible gas concentration-indicating controller 32.

In the embodiment shown in FIG. 8, when the treated wastes contain polyvinyl chloride, the concentration of hydrogen chloride gas is detected for controlling the microwave output, as well as protecting the apparatus and taking a measure against the exhaust gases, in place of the detection of the concentration of combustible gases in the embodiment shown in FIG. 6.

In some cases, the microwave output is controlled by combination of detection of the concentration of combustible gases and detection by the power monitor.

The other members and function are the same as those in the embodiment shown in FIG. 6.

In the above description, "control of the microwave output" involves ON-OFF control of microwaves.

The present invention configured as described above has the following effects:

(1) It is possible to prevent secondary infection by heat-sterilizing infectious medical implements waste and make hospitals and the like conform to the guide line of the Welfare Ministry of Japan that wastes must be sterilized in hospitals and the like, as a general rule. It is also possible to significantly reduce the payment to an industrial waste disposal firm. In Japan, as after April in 1990, the waste disposal firm receives infectious wastes at a cost of 280 to 500 yen/kg and non-infectious wastes at a cost of 20 to 30 yen/kg.

(2) When the volume of wastes is reduced by compression, melted or softened plastics are employed as an adhesive for compression molding so that injection needles and the like can be sealed in the compressed product (because the melted or softened plastics spread during compression), and attempts can be made to significantly reduce the volume and improve the handling properties.

(3) Although the apparatus for treating plastic wastes disclosed in Japanese Patent Examined Publication No. 51-25470 has the compression cylinder wall, the present invention requires no cylinder. It is therefore unnecessary to take a measure against the adhesion of the treated wastes to the cylinder wall, resulting in the ease of maintenance of the apparatus.

(4) In the embodiments shown in FIGS. 6, 7 and 8, the occurrence of local overheating can be correctly detected in an early stage by using the means for detecting a change (increase) in the concentration of combustible gases in the exhaust gases, a change in the concentration of hydrogen chloride gas in the exhaust gases and/or a change in the ratio of reflected power to incident power. The microwave heating having the characteristic that the treated wastes are heated from the inside thereof can thus be utilized to the upmost limit. This enables the treated wastes to be heated to a predetermined temperature for a shortest time by uniformly heating the whole wastes by circulating hot air, while preventing the occurrence of overheating in the treated wastes. The sterilizing effect of microwaves themselves can also be effectively utilized.

What is claimed is:

1. A method of treating medical implements waste which contains plastics comprising heat-sterilizing medical implements waste by circulating air heated to a temperature of 140° to 200° C. and applying microwaves to said medical implements waste, and controlling the output of said microwaves by detecting the concentration of combustible gases generated from said medical implements waste.

2. A method of treating medical implements waste according to claim 1, wherein the air is heated to a temperature of 140° C. to 200° C. which exceeds a softening point of plastics contained in said medical implements waste wherein a part or the whole of said plastics is melted or softened by heat-sterilization, and then compressing the waste to reduce the volume thereof.

3. A method of treating medical implements waste which contains plastics comprising heat-sterilizing medical implements waste by circulating air heated to a temperature of 140° to 200° C. and applying microwaves to said medical implements waste, and controlling the output of said microwaves by detecting a ratio between reflected power and incident power using a power monitor.

4. A method of treating medical implements waste according to claim 3, wherein the air is heated to a temperature of 140° to 200° C. which exceeds a softening point of plastics contained in said medical implements waste wherein part or the whole of said plastics is melted or softened by heat-sterilization, and then compressing the waste to reduce the volume thereof.

5. A method of treating medical implements waste comprising heat-sterilizing medical implements waste by circulating air heated to a temperature of 140° to 200° C., applying microwaves to said medical implements waste, and controlling the output of said microwaves by detecting the concentration of hydrogen chloride gas generated from the waste.

6. A method of treating medical implements waste according to claim 5, wherein part or the whole of said medical implements waste is melted or softened by heat-sterilization and is compressed for reducing the volume thereof.

7. An apparatus for treating medical implements waste comprising:
a closed apparatus body provided with an open-close door and an exhaust port;
a medical implements waste container disposed in said closed apparatus body;
a microwave generator connected to said closed apparatus body for applying microwaves to said medical implements waste container;
a heated air circulating line whose ends are connected to said closed apparatus body and having a heater and a circulating blower, both of which are provided for heating said medical implements waste container;
a compression device for compressing said medical implements waste container containing the medical implements waste so as to reduce the volume thereof;
a combustible gas concentration-indicating controller or a combustible gas concentration controller provided on an exhaust gas conduit connected to said exhaust port; and
a control unit connected to said combustible gas concentration-indicating controller or said combustible gas concentration controller and said microwave generator so as to control said microwave generator on the basis of the concentration of combustible gases.

8. An apparatus for treating medical implements waste comprising:
a closed apparatus body provided with an open-close door and an exhaust port;
a medical implements waste container disposed in said closed apparatus body;
a microwave generator connected to said closed apparatus body for applying microwaves to said medical implements waste container;
a heated air circulating line whose ends are connected to said closed apparatus body and having a heater and a circulating blower, both of which are provided for heating said medical implements waste container;
a compression device for compressing said medical implements waste container containing the medical implements waste so as to reduce the volume thereof;
a power monitor connected to a waveguide of said microwave generator; and
a control unit connected to said power monitor and said microwave generator so as to control said microwave generator on the basis of the ratio of reflected power to incident power, which ratio is detected by said power monitor.

9. An apparatus for treating medical implements waste comprising:
a closed apparatus body provided with an open-close door and an exhaust port;
a medical implements waste container disposed in said closed apparatus body;
a microwave generator connected to said closed apparatus body so as to apply microwaves to said medical implements waste container;
a heated air circulating line whose ends are connected to said closed apparatus body and having a heater and a circulating blower, both of which are provided for heating said medical implements waste container;
a compression device for compressing said medical implements waste container containing the medical implements waste so as to reduce the volume thereof;
a hydrogen chloride gas concentration-indicating controller or hydrogen chloride gas concentration controller provided on an exhaust gas conduit connected to said exhaust port; and
a control unit connected to said hydrogen chloride gas concentration-indicating controller or hydrogen chloride gas concentration controller and said microwave generator so as to control said microwave generator on the basis of the concentration of hydrogen chloride gas.

* * * * *